United States Patent
Samsoondar

(10) Patent No.: US 9,821,307 B2
(45) Date of Patent: Nov. 21, 2017

(54) SAMPLE VOLUME METERING SYSTEM FOR POINT-OF-CARE TESTING

(71) Applicant: James Samsoondar, Markham (CA)

(72) Inventor: James Samsoondar, Markham (CA)

(73) Assignee: INVIDX CORP., Markham, Ontario (CA)

( * ) Notice: Subject to any disclaimer, the term of this patent is extended or adjusted under 35 U.S.C. 154(b) by 0 days.

(21) Appl. No.: 15/356,630

(22) Filed: Nov. 20, 2016

(65) Prior Publication Data

US 2017/0144146 A1    May 25, 2017

Related U.S. Application Data

(60) Provisional application No. 62/258,520, filed on Nov. 22, 2015.

(51) Int. Cl.
| | | |
|---|---|---|
| *B01L 3/00* | (2006.01) | |
| *G01N 33/86* | (2006.01) | |
| *G01N 33/49* | (2006.01) | |

(52) U.S. Cl.
CPC .............. *B01L 3/502* (2013.01); *G01N 33/49* (2013.01); *G01N 33/86* (2013.01); *B01L 2200/025* (2013.01); *B01L 2200/0684* (2013.01); *B01L 2300/042* (2013.01); *B01L 2300/043* (2013.01); *B01L 2300/046* (2013.01); *B01L 2300/0816* (2013.01); *B01L 2300/0867* (2013.01); *B01L 2300/0887* (2013.01); *B01L 2400/0487* (2013.01); *B01L 2400/0688* (2013.01)

(58) Field of Classification Search
CPC ............. Y10T 436/2575; Y10T 436/11; Y10T 436/25; B01L 2200/10; B01L 2300/045; B01L 2300/0816; B01L 2300/0867; B01L 2300/087; B01L 3/502
See application file for complete search history.

(56) References Cited

U.S. PATENT DOCUMENTS

| | | | |
|---|---|---|---|
| 6,750,053 B1 | 6/2004 | Opalsky | |
| 7,682,833 B2* | 3/2010 | Miller | ............... B01L 3/502707 422/537 |
| 2010/0196908 A1* | 8/2010 | Opalsky | .................... B01L 7/52 435/6.1 |

* cited by examiner

*Primary Examiner* — Sally Merkling

(74) *Attorney, Agent, or Firm* — Gowling WLG (Canada) LLP

(57) ABSTRACT

Some embodiments of the invention provide a disposable cartridge for rapidly metering a sample for measuring a property of the sample. The cartridge can receive a sample when it is in an unsealed configuration, and a cap is used to facilitate metering of the sample and sealing the cartridge. When the cartridge is in a sealed configuration, pressurised air is used to push the metered sample into a chamber containing at least one reagent, and subsequently into a detection chamber for measuring the property of the sample.

20 Claims, 10 Drawing Sheets

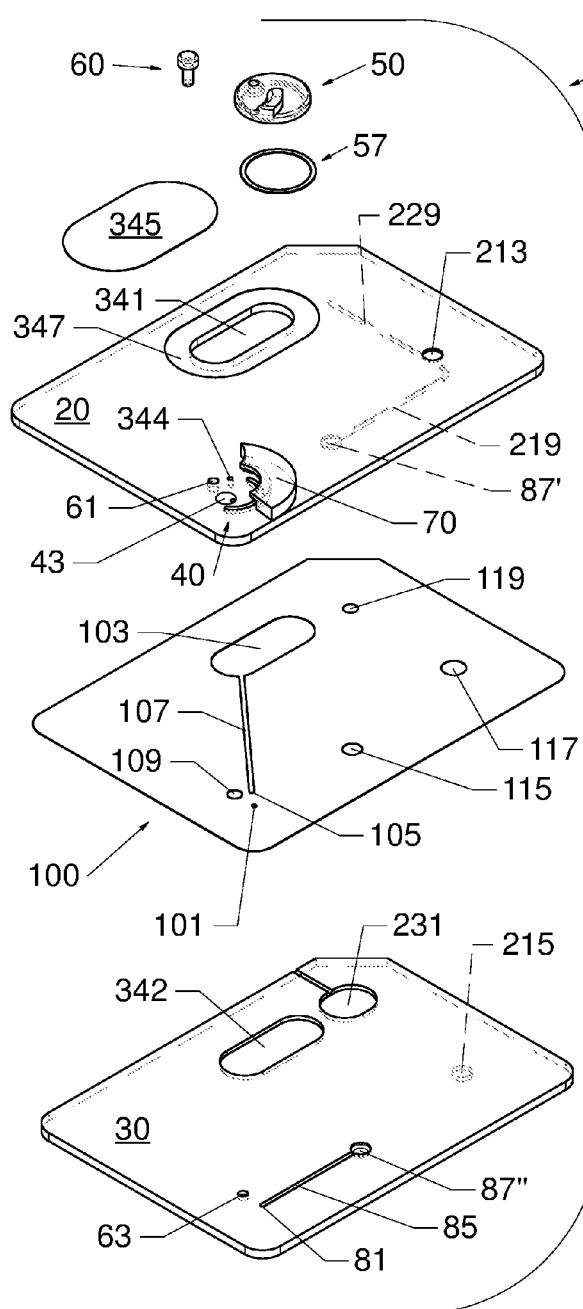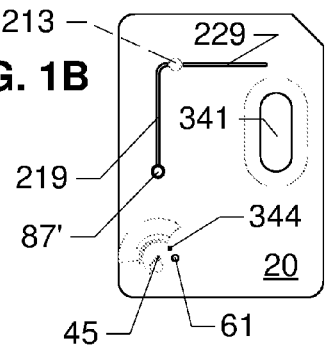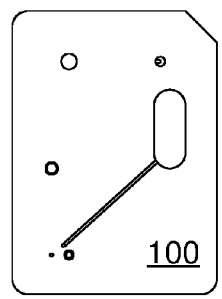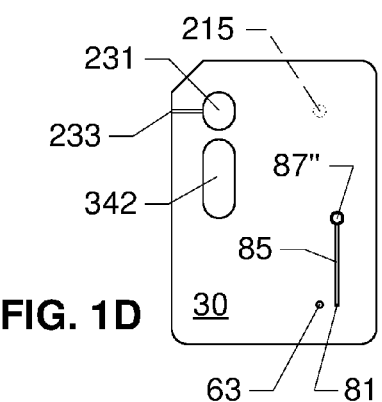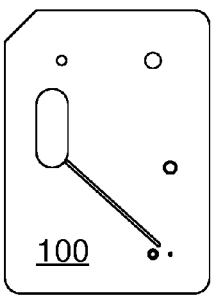

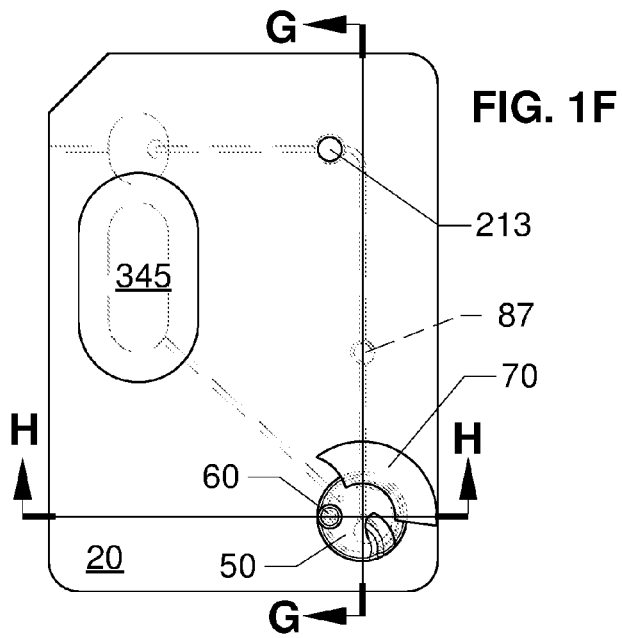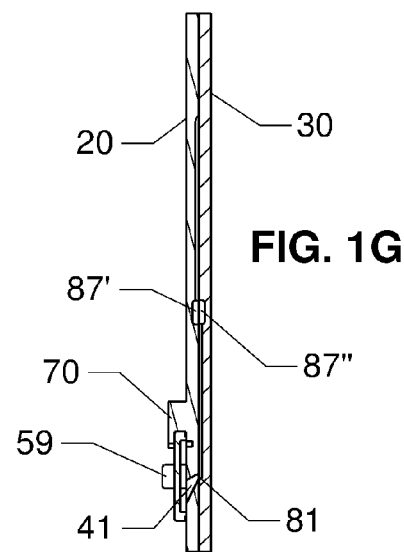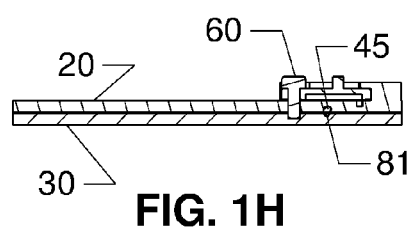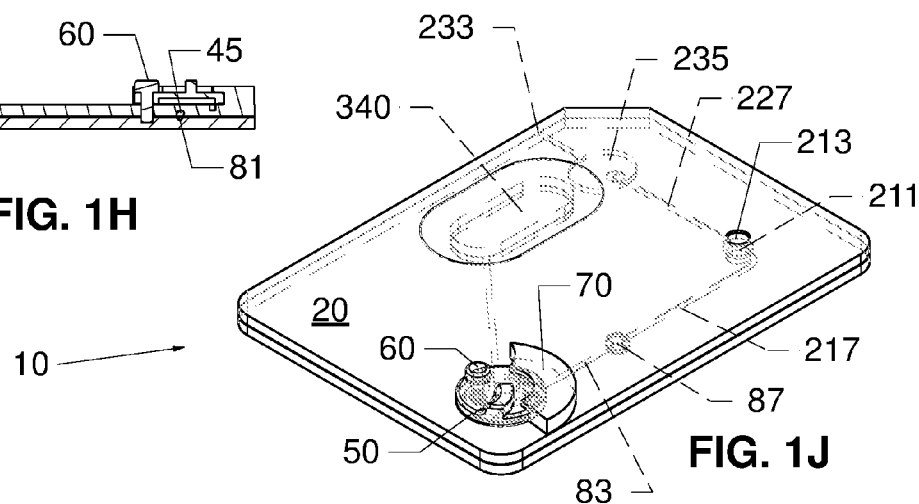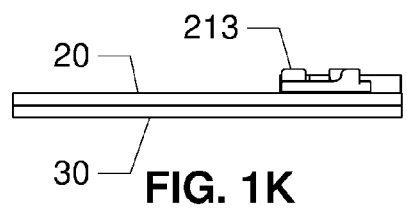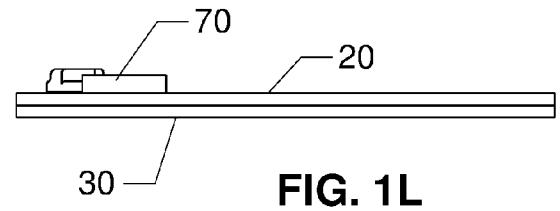

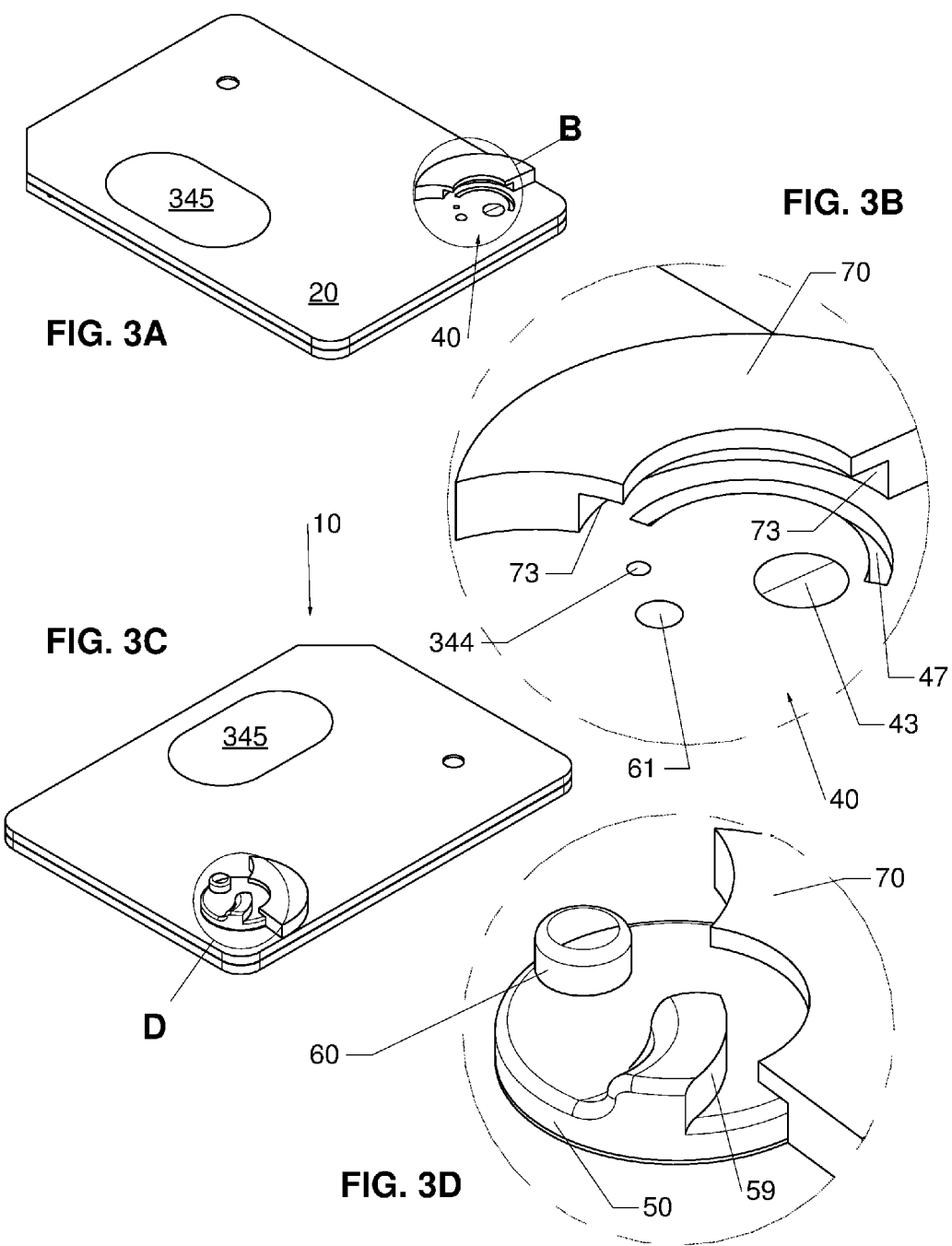

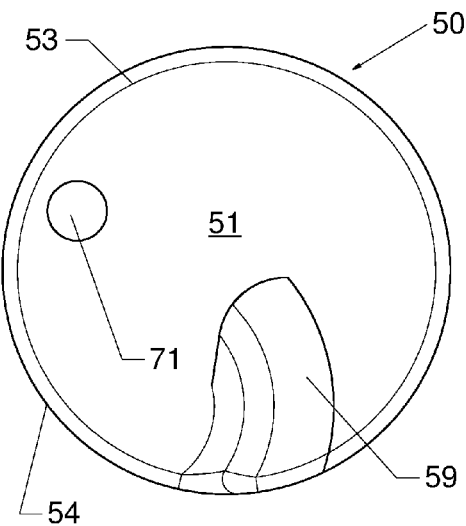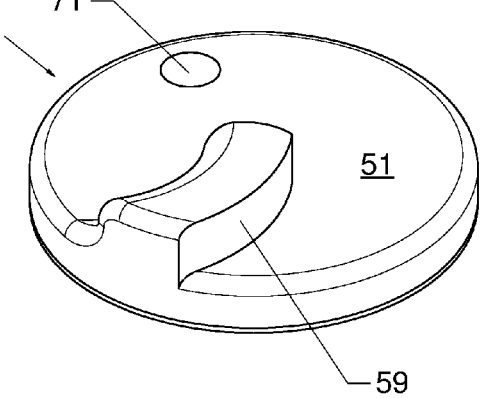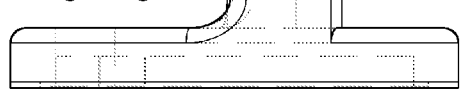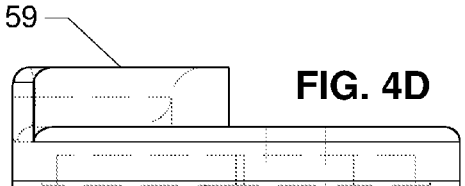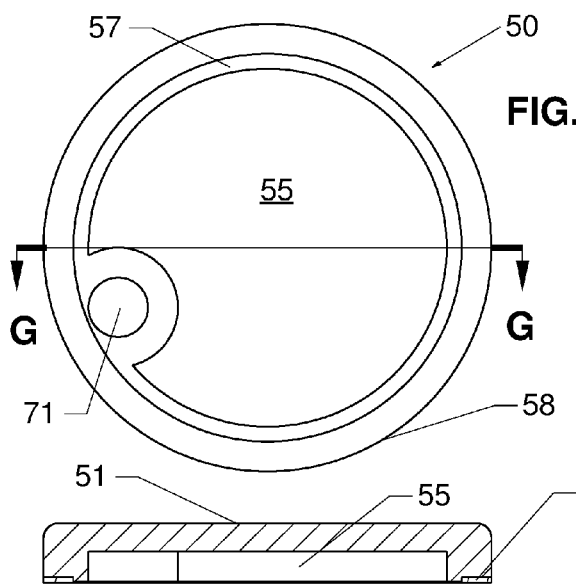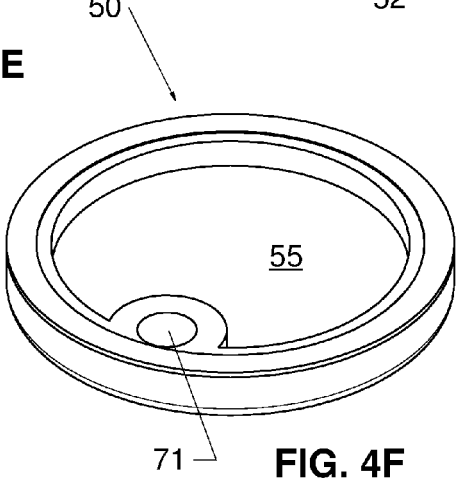

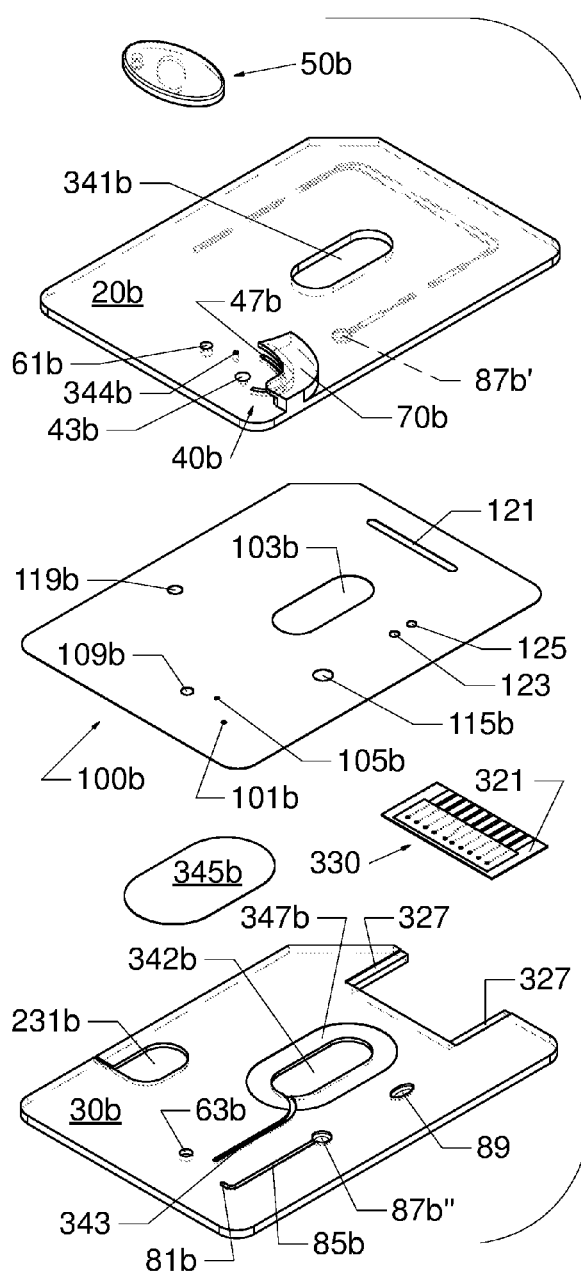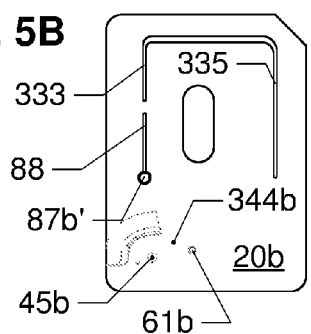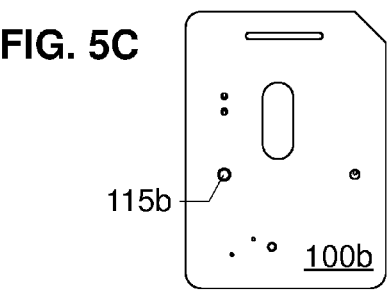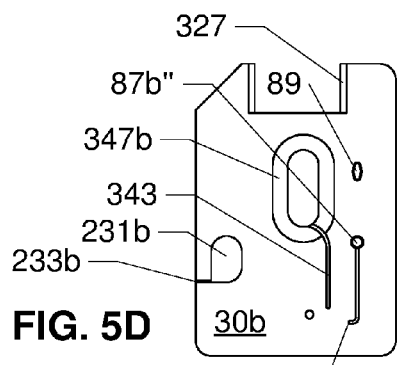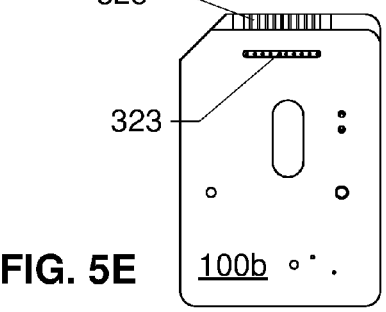

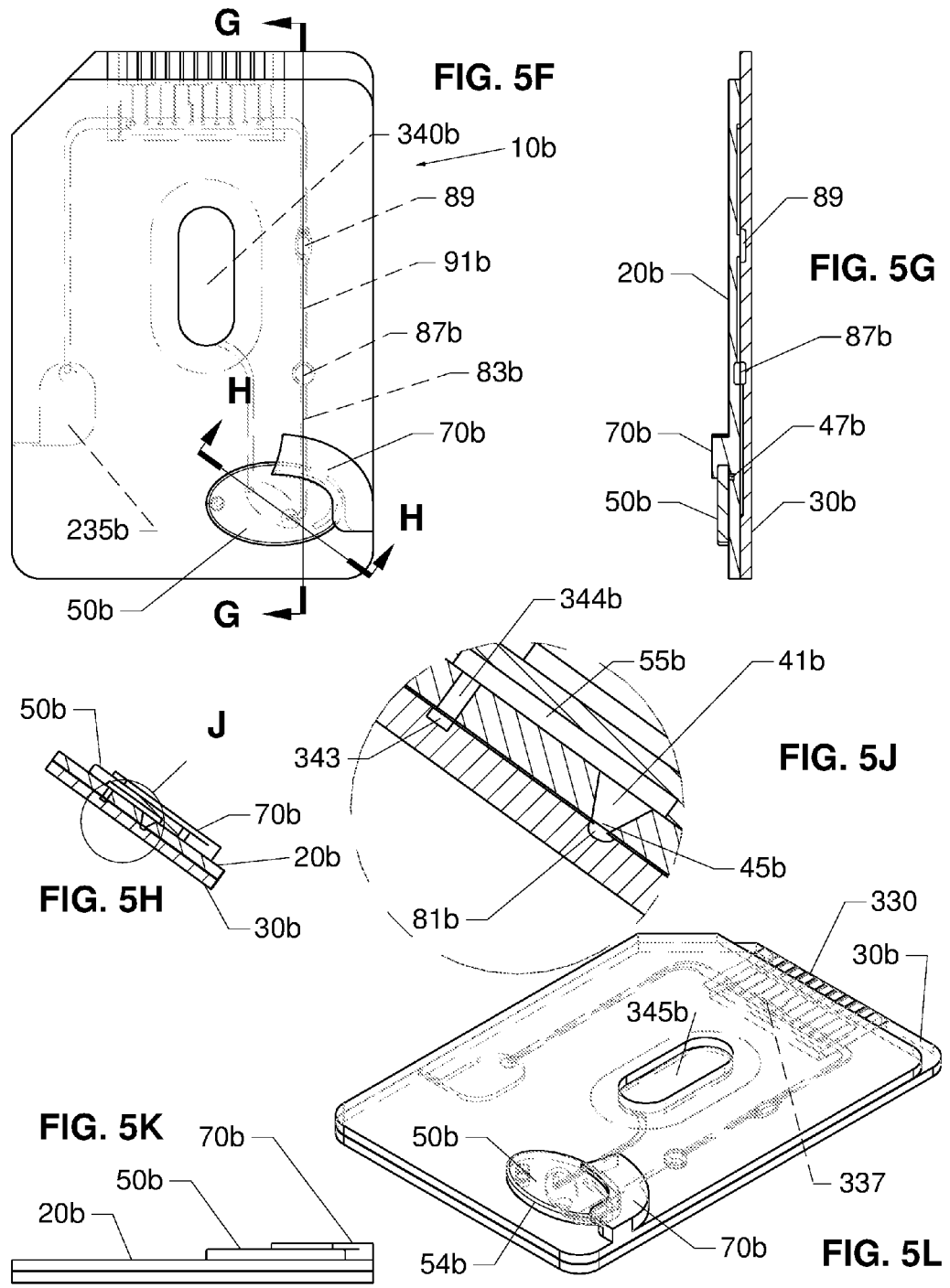

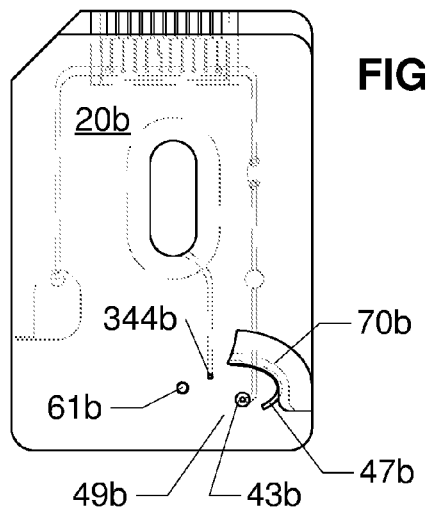
FIG. 6A
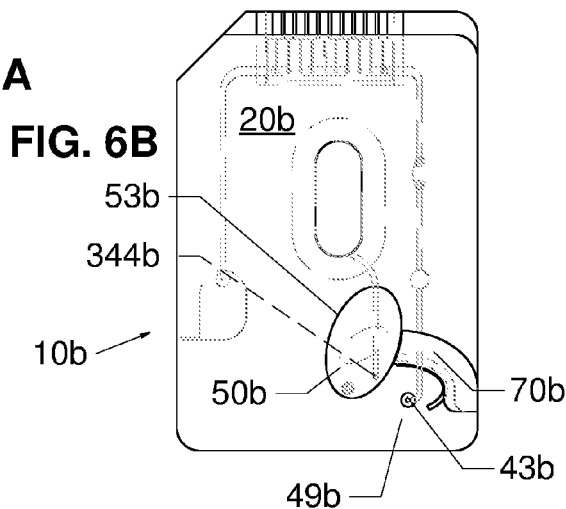
FIG. 6B
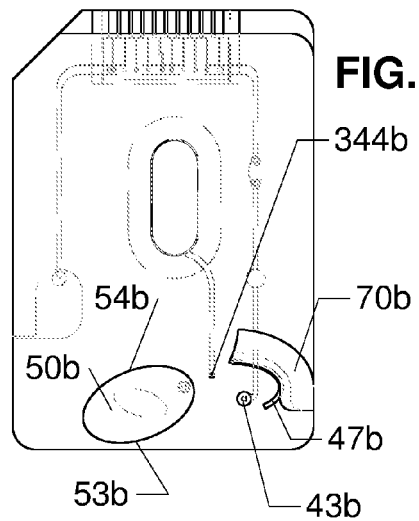
FIG. 6C
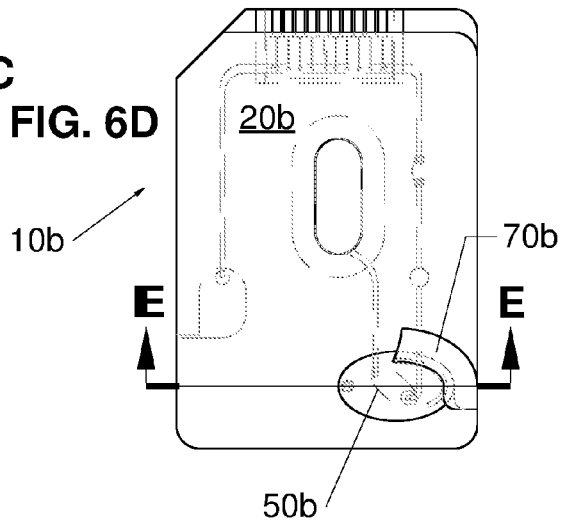
FIG. 6D
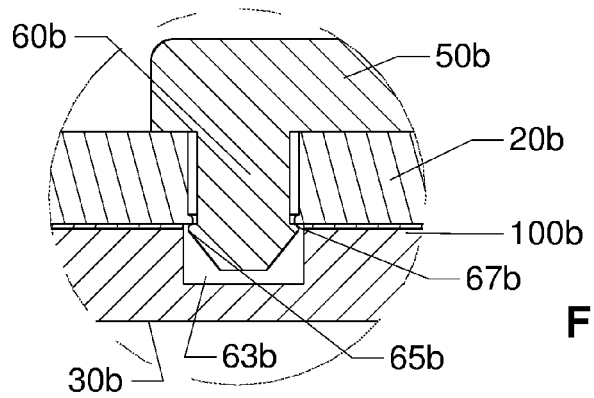
FIG. 6E
FIG. 6F

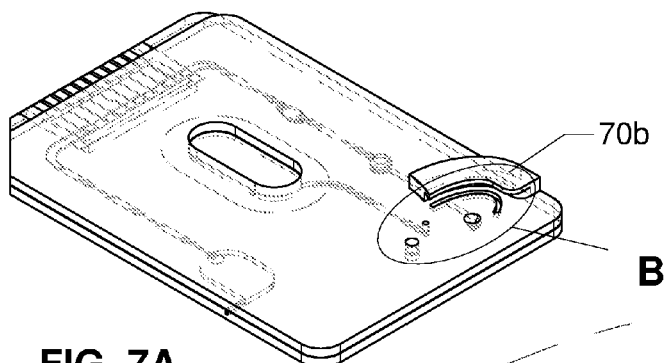
FIG. 7A
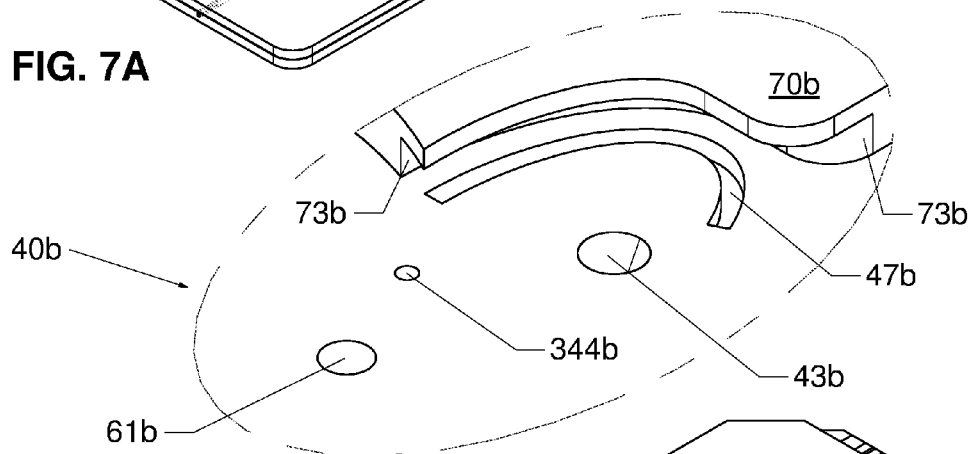
FIG. 7B
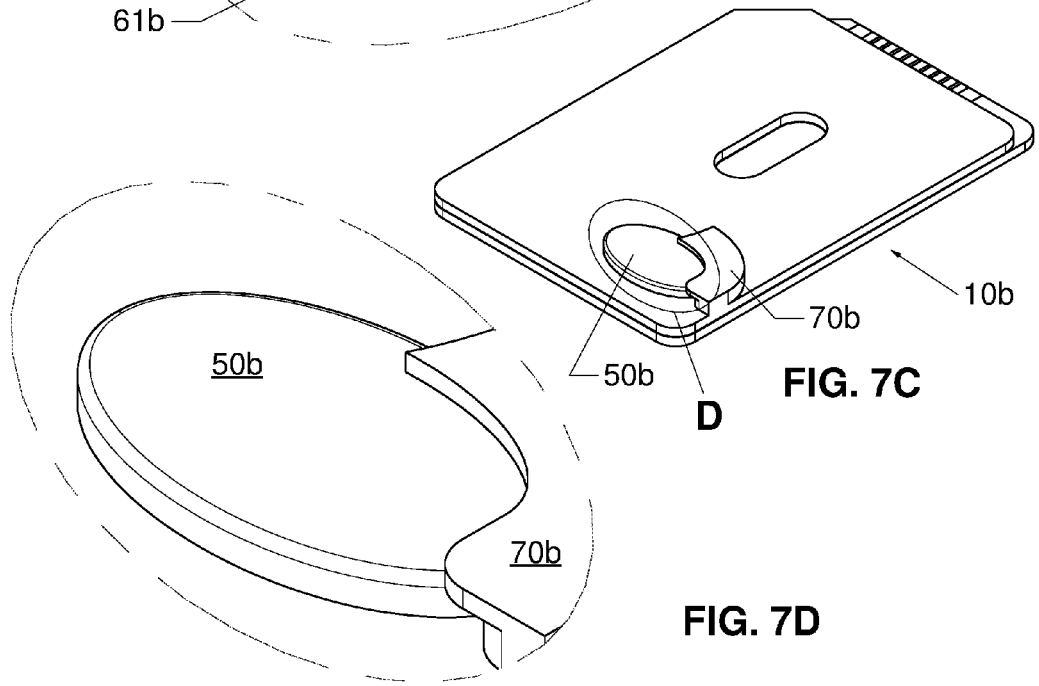
FIG. 7C
FIG. 7D

FIG. 8A
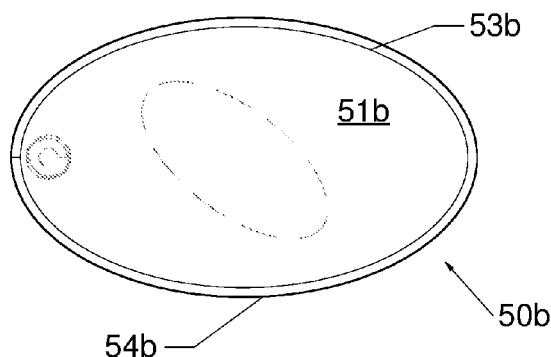
FIG. 8B
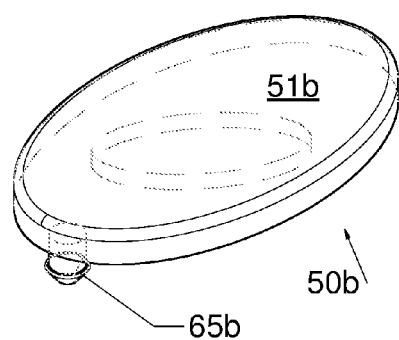
FIG. 8C
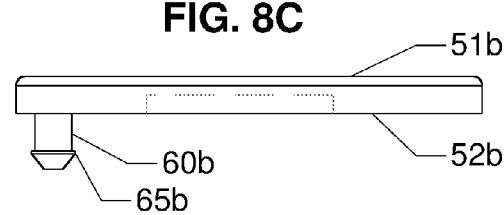
FIG. 8D
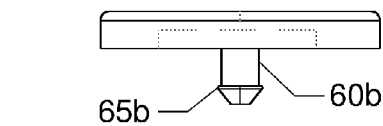
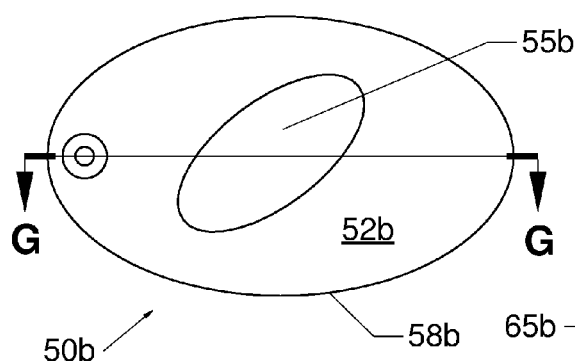
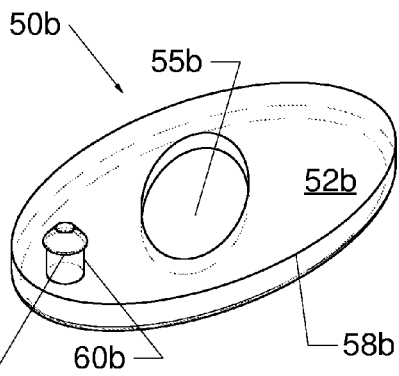
FIG. 8E
FIG. 8F
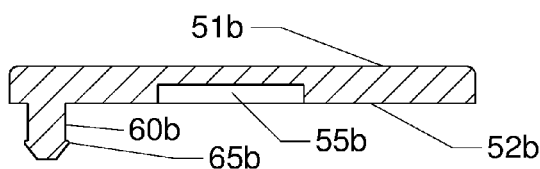
FIG. 8G

US 9,821,307 B2

SAMPLE VOLUME METERING SYSTEM FOR POINT-OF-CARE TESTING

RELATED APPLICATIONS

The application is a continuation of U.S. Provisional Patent Application No. 62/258,520, filed on Nov. 22, 2015, which is hereby incorporated by reference.

FIELD OF THE INVENTION

The invention relates to a rapid sample volume metering system for measuring a property of the sample. The system is particularly useful for point-of-care testing (POCT) that requires a certain volume of blood, but the sample provided is for example, a pin-prick drop of blood having an unknown volume.

BACKGROUND OF THE INVENTION

The result of reaction between a liquid sample and one or more reagent, preferably dry, depends on the quantity of the one or more reagent and the volume of liquid sample. Although any type of liquid sample is implied, serum, plasma and blood (also referred to as whole blood) are samples of particular interest. When blood is allowed to clot and the sample is centrifuged, the yellow liquid that sits on top of the blood clot is called serum. If the blood is collected in a tube containing an anticoagulant, for example heparin, and the sample is centrifuged, the yellow liquid that sits on top of the packed red blood cells is called plasma. The packed cell volume (PCV) or hematocrit determines the percentage of red blood cells (RBCs) in whole blood. Since only the RBCs contain hemoglobin, total hemoglobin is highly correlated with hematocrit, except in cases of for example, macrocytic anemia. Some analyzers measure hematocrit by electrical conductivity, and convert the hematocrit measurement to a total hemoglobin concentration, and some analyzers measure total hemoglobin concentration by spectroscopy, and convert the total hemoglobin concentration to a hematocrit value. Spectroscopic calibration algorithms can be developed to measure both hematocrit and total hemoglobin concentration.

Point-of-care Testing (POCT) is defined as medical diagnostic testing performed outside the clinical laboratory in close proximity to where the patient is receiving care. POCT is typically performed by non-laboratory personnel and the results are used for clinical decision making. For the sake of convenience and rapid turnaround time, blood is the sample of choice. Due to the complexity of blood, certain tests can only be performed on serum or plasma.

POCT has a range of complexity and procedures that vary from manual procedures to automated procedures conducted by portable analyzers. POCT is most efficient when the sample of interest can be applied to or loaded onto a test cartridge, the sample inlet capped, and the remaining steps are performed automatically after the loaded test cartridge is inserted into a slot or receptor of an analyzer. Some blood tests, for example coagulation assays and immunoassays require a fixed volume of sample whereas other tests for example electrolytes, do not require a fixed volume of sample. In the case of electrolytes, sample volume may not be an issue if the electrolyte concentration is estimated by measuring electrical activity in the sample. The present invention relates to a point-of-care testing system with automatic sample volume metering, subsequent to applying an unknown sample volume to a disposable cartridge.

Applying an unmetered sample volume to test strips is well known; some test strips contain absorbing sections that can accommodate a known volume of plasma, after the red cells are retained in another section of the test strip near the blood application site. In some cases, the hematocrit affects the plasma flow in test strips, and therefore correction for hematocrit may improve accuracy of the analyte measurement. In some systems, a pipette is used that is designed to dispense a predetermined sample volume, after aspirating excess sample into the pipette.

U.S. Pat. No. 6,750,053 to Opalsky et al and U.S. Pat. No. 7,682,833 to Miller et al disclose devices for rapidly metering samples. U.S. Pat. No. 6,750,053 describes a snap-shut seal and discloses in column 11 lines 16-19: "The volume of the metered fluid sample is the volume of the holding chamber 20 between the orifice (48 in FIG. 5) in the wall of the holding chamber and the capillary stop 22." U.S. Pat. No. 7,682,833 discloses in column 23 lines 39-43: "The location at which air enters the sample chamber (gasket hole 27) from the bladder, and the capillary stop 25, together define a predetermined volume of the sample chamber. An amount of the sample corresponding to this volume is displaced into the first conduit when paddle 6 is depressed." In the cases of U.S. Pat. No. 6,750,053 and U.S. Pat. No. 7,682,833, the sample in the sample collection well (illustrated in U.S. Pat. No. 6,750,053 as element 12 in FIG. 3) is wasted.

Sample size is a major consideration for POCT systems, especially when it is desirable to use a small drop of blood obtained by puncturing the skin of a body part; the sample is referred to as a pin-prick sample. With some patients, it is difficult to obtain a small drop of blood, therefore there is a need to avoid any blood wastage. This is particularly true for neonatal testing. The present invention overcomes the disadvantage of sample wastage by providing a novel sample volume metering system.

SUMMARY OF THE INVENTION

In accordance with an aspect of an embodiment of the present invention, there is provided a disposable cartridge for metering a sample for measuring a property of the sample. The cartridge comprises a cap having a sweeping edge for skimming off excess sample, a top side and an underside comprising a flat surface and a recess. The cartridge also comprises a sample inlet portion having: a sample storage well for storing a portion of the sample, the storage well comprising a top portion for receiving the sample and a bottom portion for releasing sample; a sliding surface for frictionally engaging the flat surface of the underside of the cap; a hole for receiving a pin for hingedly attaching the cap; and a sample storage conduit for receiving some of the sample from the bottom portion of the sample storage well, the sample storage conduit terminating at a capillary break; a detection chamber for receiving sample from the capillary break for generating a signal used to calculate the property of the sample; and an air bladder having an arrangement with the air bladder exit port and the cap recess when the cartridge is in the sealed configuration for providing pressurized air to the sample storage well for urging the sample into the detection chamber. When the cartridge is in the sealed configuration, the volume of sample is defined by the combined volumes of the sample storage well and the sample storage conduit. In some embodiments of the cartridge, the top portion of the sample storage well is substantially larger than the bottom portion of the sample storage well. In some embodiments of the cartridge, the pin is an integral part of the cap and in other embodiments, the pin is a separate element. In other embodiments of the cartridge, at least one of the sample storage conduit and the capillary break comprises at least one reagent. Other embodiments of the cartridge comprise a mixing chamber positioned between the capillary break and the detection chamber, the mixing chamber optionally comprising at least one reagent.

In accordance with another aspect of an embodiment of the present invention, there is provided a disposable cartridge for metering a sample for measuring a property of the sample, the cartridge comprising a cap and a housing. The cap comprises a sweeping edge for skimming off excess sample, a top side, and an underside, the underside comprising a flat surface and a recess enclosed by the flat surface. The housing comprises: a sample storage well for storing a portion of the sample, the storage well comprising a top portion for receiving the sample and a bottom portion for releasing sample; a hole for receiving a pin for hingedly attaching the cap to the housing; a sample storage conduit for receiving some of the sample from the bottom portion of the sample storage well, the sample storage conduit terminating at a capillary break; a detection chamber for receiving sample from the capillary break and for generating a signal used to calculate the property of the sample; an air bladder exit port; an air bladder having an arrangement with the air bladder exit port for providing pressurized air to the sample storage well for urging the sample into the detection chamber; and a vent for relieving pressure in the detection chamber. The cartridge is adjustable between an unsealed configuration and the sealed configuration, facilitated by the pin. In the unsealed configuration, and not in the sealed configuration, the sample storage well is configured to receive the sample. In the sealed configuration, and not in the unsealed configuration, the cap recess facilitates provision of a closed air passage connecting the air bladder exit port and the sample storage well for communicating the pressurized air from the air bladder exit port to the sample storage well. The volume of sample in the cartridge in the sealed configuration is equivalent to the volume measured from the top portion of the sample storage well to the capillary break. Some embodiments further comprise a latch for securing the cap when the cartridge is in a sealed configuration, and some embodiments comprise a sample overflow well for receiving excess sample. In some embodiments, instead of the overflow well, there is a groove disposed at the underside of the cap in front of the sweeping edge of the cap, for holding the excess sample.

In accordance with yet another aspect of an embodiment of the present invention, there is provided a system for metering a sample for measuring a property of the sample. The system comprises a cartridge and an analyzer. The cartridge comprises a cap and a housing. The cap comprises a sweeping edge for skimming off excess sample, a top side, and an underside, the underside having a recess. The housing comprises: a sample storage well for storing a portion of the sample, the storage well comprising a top portion for receiving the sample and a bottom portion for releasing sample; a hole for receiving a pin for hingedly attaching the cap to the housing; a sample storage conduit for receiving some of the sample from the bottom portion of the sample storage well, the sample storage conduit terminating at a capillary break; a detection chamber for receiving sample from the capillary break and for providing signal to the analyzer for measuring the property of the sample; an air bladder exit port; an air bladder having an arrangement with the air bladder exit port for providing pressurized air to the sample storage well for urging the sample into the detection chamber; and a vent for relieving pressure in the detection chamber. The analyzer comprises: a receptor for receiving the cartridge; a processor for controlling the analyzer; means for activating the air bladder, for example a stepper motor; and means for receiving the signal from the detection chamber and calculating the property of the sample. The description provides as examples of detection technology, optical measurement and electrochemical sensors, but these are examples only and other forms of generating signals and receiving generated signals for measuring an analyte are considered to be within the scope of the present invention.

Other aspects and features of the present invention will become apparent, to those having ordinary skill in the art, upon review of the following description of specific embodiments of the invention, which are provided as examples.

BRIEF DESCRIPTION OF THE DRAWINGS

A better understanding of the novel features and advantages of present invention will be made by reading the detailed description of the preferred embodiments provided later, in conjunction with the accompanying drawings, in which:

FIG. 1A is an exploded view of the disposable cartridge 10 for measuring a property of a sample, the cartridge having a rapid sample metering system, according to a first embodiment of the cartridge;

FIG. 1B is a bottom view of the first housing member 20 of the cartridge shown in FIG. 1A;

FIG. 1C is the bottom view of the first housing member 20 of the cartridge shown in FIG. 1B, overlaid by and in alignment with the gasket 100 shown in FIG. 1A;

FIG. 1D is a top view of the second housing member 30 of the cartridge shown in FIG. 1A;

FIG. 1E is the top view of the second housing member 30 shown in FIG. 1D, overlaid by and in alignment with the gasket 100 shown in FIG. 1A;

FIG. 1F is a top view of the cartridge 10 shown in FIG. 1A, with the cap 50 in a fully closed position;

FIG. 1G is a first cross-sectional view through the cartridge shown in FIG. 1F along line G-G;

FIG. 1H is a second cross-sectional view through the cartridge shown in FIG. 1F along line H-H;

FIG. 1J is a perspective view of the cartridge shown in FIG. 1A and FIG. 1F;

FIG. 1K is a front view of the cartridge shown in FIG. 1F;

FIG. 1L is a right side view of the cartridge shown in FIG. 1F;

FIG. 3A is a perspective view of the cartridge 10 shown in FIG. 2A;

FIG. 3B is a detailed view of detail B of the cartridge shown in FIG. 3A, showing details of the sample inlet portion 40;

FIG. 3C is a perspective view of the cartridge 10 shown in FIG. 2D;

FIG. 3D is a detailed view of detail D of the cartridge shown in FIG. 3C;

FIG. 4A is a top view of the cap 50 shown in FIGS. 2B-2D;

FIG. 4B is a perspective view of the cap 50 shown in FIG. 4A;

FIG. 4C is a front view of the cap 50 shown in FIG. 4A;

FIG. 4D is a right side view of the cap 50 shown in FIG. 4A;

FIG. 4E is a bottom view of the cap 50 shown in FIG. 4A;

FIG. 4F is a perspective view of the cap 50 shown in FIG. 4E;

FIG. 4G is a cross-sectional view through the cap 50 shown in FIG. 4E along line G-G;

FIG. 5A is an exploded view of the disposable cartridge 10b for measuring a property of a sample, the cartridge having a rapid sample metering system, according to a second embodiment of the cartridge;

FIG. 5B is a bottom view of the first housing member 20b of the cartridge shown in FIG. 5A;

FIG. 5C is the bottom view of the first housing member 20b shown in FIG. 5B, overlaid by and in alignment with the gasket 100b shown in FIG. 5A;

FIG. 5D is a top view of the second housing member 30b of the cartridge shown in FIG. 5A;

FIG. 5E is the top view of the second housing member 30b shown in FIG. 5D, overlaid by and in alignment with the gasket 100b shown in FIG. 5A;

FIG. 5F is a top view of the cartridge 10b shown in FIG. 5A, with the cap 50b in a fully closed position;

FIG. 5G is a first cross-sectional view through the cartridge 10b shown in FIG. 5F along line G-G;

FIG. 5H is a second cross-sectional view through the cartridge 10b shown in FIG. 5F along line H-H;

FIG. 5J is a detailed view of detail J of the cartridge 10b shown in FIG. 5H, showing the fluid connection between the air bladder exit port 344b and sample well 41b, via cap recess 55b;

FIG. 5K is a front view of the cartridge 10b shown in FIG. 5F;

FIG. 5L is a perspective view of the cartridge 10b shown in FIG. 5F;

FIG. 6A is a top view of the cartridge 10b shown collectively in FIGS. 5A-5L, with the cap 50b hidden;

FIG. 6B is a top view of the cartridge 10b shown collectively in FIGS. 5A-5L, with the cap 50b in a fully open position;

FIG. 6C is a top view of the cartridge 10b shown collectively in FIGS. 5A-5L, with the cap 50b in a partly open position;

FIG. 6D is a top view of the cartridge 10b shown collectively in FIGS. 5A-5L, with the cap 50b in a fully closed position;

FIG. 6E is a cross-sectional view of cartridge 10b shown in FIG. 6D along line E-E;

FIG. 6F is a detailed view of detail F of cartridge 10b shown in FIG. 6E, showing a snap-fit mechanism for engaging the cap 50b in the cartridge;

FIG. 7A is a perspective view of the cartridge 10b (with the cap 50b hidden) shown in FIG. 6A;

FIG. 7B is a detailed view of detail B of the cartridge shown in FIG. 7A, showing details of the sample inlet portion 40b;

FIG. 7C is a perspective view of the cartridge 10b shown in FIG. 6D;

FIG. 7D is a detailed view of detail D of the cartridge shown in FIG. 7C;

FIG. 8A is a top view of the cap 50b shown in FIG. 7C;

FIG. 8B is a perspective view of the cap 50b shown in FIG. 8A;

FIG. 8C is a front view of the cap 50b shown in FIG. 8A;

FIG. 8D is a right side view of the cap 50b shown in FIG. 8A;

FIG. 8E is a bottom view of the cap 50b shown in FIG. 8A;

FIG. 8F is a perspective view of the cap 50b shown in FIG. 8E; and

FIG. 8G is a cross-sectional view through the cap 50b shown in FIG. 8E along line G-G.

Figure 2A:
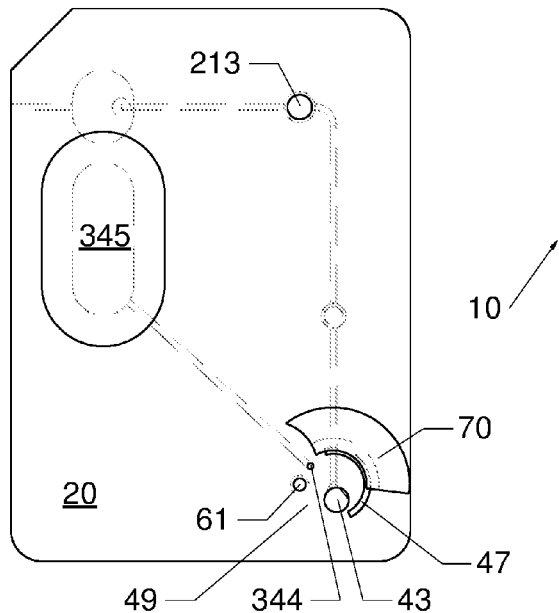
FIG. 2A is a top view of the cartridge 10 shown collectively in FIGS. 1A-1L, with the cap 50 and pin 60 hidden.

For a better understanding of the present invention, and to show more clearly how it may be carried into effect, reference will now be made, by way of example, to the accompanying drawings, and which are described in the following detailed description of preferred aspects of the invention.

DETAILED DESCRIPTION OF PREFERRED ASPECTS OF THE INVENTION

Detailed description of novel features of preferred embodiments of the invention is discussed now, and is best understood with reference to the accompanying drawings. These embodiments are examples only, and a person of ordinary skill in the art will understand that other embodiments are within the scope of the invention, even though they are not explicitly illustrated. Attempts are made to use the same reference numerals for similar elements in different embodiments; in some cases letters are appended to the end of the reference numerals to denote the embodiment of the invention illustrated. For example, the letter b is used to refer to the $2^{nd}$ embodiment of the invention. It should be noted that absence of a letter does not imply that the embodiment is the first embodiment of the invention, for example only the second embodiment illustrates use of a biosensor array for the detection and is referred to as 330. For easy reference, Table 1 provides a list of the reference numerals used, and a brief description of the corresponding structural features.

TABLE 1

| Reference Numerals | Description of Structural Features |
| --- | --- |
| 10 | A first embodiment of a cartridge |
| 10b | A second embodiment of a cartridge |
| 20 | First housing member of cartridge 10 |
| 20b | First housing member of cartridge 10b |
| 30 | Second housing member of cartridge 10 |
| 30b | Second housing member of cartridge 10b |
| 40 | A sample inlet portion of cartridge 10 |
| 40b | A sample inlet portion of cartridge 10b |
| 41 | A sample storage well of an inlet portion 40 |
| 41b | A sample storage well of an inlet portion 40b |
| 43 | Top portion of a sample storage well 41 |
| 43b | Top portion of a sample storage well 41b |
| 45 | Bottom portion of sample storage well 41 |
| 45b | Bottom portion of sample storage well 41b |
| 47 | A sample overflow well of an inlet portion 40 |
| 47b | A sample overflow well of an inlet portion 40b |
| 49 | A sliding surface of inlet portion 40 |
| 49b | A sliding surface of inlet portion 40b |
| 50 | A cap for closing inlet portion 40 of cartridge 10 |
| 50b | A cap for closing inlet portion 40b of cartridge 10b |
| 51 | Top side of cap 50 |
| 51b | Top side of cap 50b |
| 52 | Underside of cap 50 |
| 52b | Underside of cap 50b |

TABLE 1-continued

| Reference Numerals | Description of Structural Features |
|---|---|
| 53 | A sweeping portion of cap 50 |
| 53b | A sweeping portion of cap 50b |
| 54 | A trailing portion of cap 50 |
| 54b | A trailing portion of cap 50b |
| 55 | Cap recess in the underside of cap 50 |
| 55b | Cap recess in the underside of cap 50b |
| 57 | A cap sealing ring/washer in cap 50 |
| 58 | A sweeping cap edge disposed at the sweeping portion 53 of cap 50 for skimming off excess sample |
| 58b | A sweeping cap edge disposed at the sweeping portion 53b of cap 50b for skimming off excess sample |
| 59 | A cap handle for facilitating rotation of cap 50 |
| 60 | A pin for hingedly attaching the cap 50 to the sample inlet portion 40 and allowing the cap to swing with the cap sealing ring/washer 57 frictionally engaged with the surface 49 of inlet portion 40 |
| 60b | A pin in cap 50b for hingedly attaching the cap to the sample inlet portion 40b and allowing the cap to swing with the non-recessed portion of the underside of the cap frictionally engaged with the surface 49b of inlet portion 40b |
| 61 | A pin hole in first housing member for receiving pin 60 |
| 61b | A pin hole for receiving pin 60b |
| 63 | Bottom of pin hole 61 |
| 63b | Bottom of pin hole 61b |
| 65b | Snap fit lip in pin for locking pin 60b in pinhole 61b |
| 67b | Snap fit lip in pinhole for locking pin 60b in pinhole 61b |
| 70 | Cap latch in inlet portion 40 |
| 70b | Cap latch in inlet portion 40b |
| 71 | Pin hole in cap 60 for receiving pin 60 |
| 73 | Cap latch recess in cap latch 70 |
| 73b | Cap latch recess in cap latch 70b |
| 81 | A sample storage conduit entrance of a cartridge 10 |
| 81b | A sample storage conduit entrance of a cartridge 10b |
| 83 | A sample storage conduit of a cartridge 10 |
| 83b | A sample storage conduit of a cartridge 10b |
| 85 | A sample storage conduit groove of a cartridge 10 |
| 85b | A sample storage conduit groove of a cartridge 10b |
| 87' | Portion of a capillary break in a first housing member of cartridge 10 |
| 87'' | Portion of a capillary break in a second housing member of cartridge 10 |
| 87 | A capillary break of a cartridge, comprising portions 87', 87'', and a gasket cut-out 115 aligned with portions 87' and 87'' |
| 87b' | Portion of a capillary break in a first housing member of cartridge 10b |
| 87b'' | Portion of a capillary break in a second housing member of cartridge 10b |
| 87b | A capillary break of a cartridge, comprising portions 87b', 87b'', and a gasket cut-out 115b aligned with portions 87b' and 87b'' |
| 88 | A mixing chamber entrance groove of cartridge 10b |
| 89 | A mixing chamber of a cartridge 10b |
| 91b | a post capillary break conduit for providing fluid communication between the capillary break 87B and the mixing chamber 89 |
| 100 | Double-sided sticky gasket of cartridge 10 |
| 100b | Double-sided sticky gasket of cartridge 10b |
| 101 | Gasket cut-out 101 positioned to provide fluid connection between a bottom of a sample storage well and a sample storage conduit entrance of a cartridge |
| 101b | Gasket cut-out 101b positioned to provide fluid connection between a bottom of a sample storage well and a sample storage conduit entrance of a cartridge |
| 103 | Gasket cut-out 103 positioned to provide fluid connection between an air bladder window and an air bladder cavity |
| 103b | Gasket cut-out 103b positioned to provide fluid connection between an air bladder window and an air bladder cavity |
| 105 | Gasket cut-out 105 positioned to provide fluid connection between an air bladder and an air bladder exit port 344 |
| 105b | Gasket cut-out 105 positioned to provide fluid connection between an air bladder duct 343b and an air bladder exit port 344b |
| 107 | Gasket cut-out 107 positioned to provide fluid connection between air bladder 340 and air bladder exit port 344b |
| 109 | Gasket cut-out 109 position to align with pin hole 61 |
| 109b | Gasket cut-out 109b position to align with pin hole 61b |
| 115 | Gasket cut-out 115 position to align with capillary break 87 |
| 115b | Gasket cut-out 115b position to align with capillary break 87b |
| 117 | Gasket cut-out 117 positioned to provide fluid connection between an optical chamber inlet conduit 217 and an optical chamber overflow conduit 227, and positioned to align with optical windows 213 and 215 |
| 119 | Gasket cut-out 119 positioned to provide fluid connection between the overflow chamber conduit 227 and a waste receptacle 235 of cartridge 10 |
| 119b | Gasket cut-out 119b positioned to provide fluid connection between the distal end of the biosensor conduit 337 and a waste receptacle 235b of cartridge 10b |
| 121 | Gasket cut-out 121 positioned to align with a portion of the biosensor conduit groove 335 and the active area 323 of the biosensor array 330 of cartridge 10b |
| 123 | Gasket cut-out 123 positioned to align with a portion of the inlet of the mixing chamber 89 of cartridge 10b |
| 125 | Gasket cut-out 125 positioned to align with a portion of the outlet of the mixing chamber 89 of cartridge 10b |
| 211 | An optical chamber in cartridge 10 for receiving sample mixed with reagent, and positioned to align with at least a portion of an optical window |
| 213 | A first optical window of cartridge 10 |
| 215 | A second optical window of cartridge 10 |
| 217 | Inlet conduit of optical chamber 211 |
| 219 | Optical inlet conduit groove of inlet conduit 217 |
| 227 | Overflow conduit optical chamber 211 |
| 229 | Overflow conduit groove of optical chamber 211 |
| 231 | A waste receptacle cavity of cartridge 10 |
| 231b | A waste receptacle cavity of cartridge 10b |
| 233 | A waste receptacle vent of cartridge 10 |
| 233b | A waste receptacle vent of a cartridge of cartridge 10b |
| 235 | A waste receptacle of cartridge 10 |
| 235b | A waste receptacle of cartridge 10b |
| 321 | Biosensor substrate for printing elements of the biosensors and for facilitating thermal contact with an analyzer heating element |
| 323 | Active area of a biosensor array |
| 325 | Biosensor electrical contact |
| 327 | A biosensor receptacle for arranging one or more biosensors in a cartridge in the form of a cut-out ledge in the second housing member, and for exposing the underside of the biosensor(s) to facilitate heating |
| 330 | A biosensor array of cartridge 10b |
| 333 | Proximal end of a biosensor conduit groove of cartridge 10b |
| 335 | Distal end of a biosensor conduit groove of cartridge 10b |
| 337 | A biosensor conduit of cartridge 10b |
| 340 | An air bladder of cartridge 10 |
| 340b | An air bladder of cartridge 10b |
| 341 | An air bladder window of an air bladder 340 |
| 341b | An air bladder window of an air bladder 340b |
| 342 | An air bladder cavity of cartridge 10 |
| 342b | An air bladder cavity of cartridge 10b |
| 343 | A groove (in member 30b) of an air bladder duct, the duct providing fluid connection between an air bladder 340b and an air bladder exit port 344b |
| 344 | An air bladder exit port of a sample inlet portion 40 |
| 344b | An air bladder exit port of a sample inlet portion 40b |
| 345 | Flexible member of a cartridge for covering air bladder window 341 of cartridge 10 for facilitating operation of the air bladder 340 |
| 345b | Flexible member of a cartridge for covering air bladder window 341b of cartridge 10b for facilitating operation of the air bladder 340b |
| 347 | Recess for nesting flexible member 345, disposed at the surface of first housing member 20 |
| 347b | Recess for nesting flexible member 345b, disposed at the surface of second housing member 30b |

Shown in FIG. 1A is an exploded view of the disposable cartridge 10 for measuring a property of a sample, the cartridge having a rapid sample metering system, according to a first embodiment of the cartridge. From top to bottom, the components are listed. The first is a pin 60 used to hingedly attach the cap 50 to the cartridge via the pin hole 61 shown in the first housing member 20; the bottom of the pin hole 61 is shown as 63 in the second housing member 30. Next is an optional cap sealing ring or washer 57, which is usually attached to the underside of the cap 50. Next is a flexible member 345, usually nested in a recess 347 in the first housing member 20 and used to seal off the air bladder window 341. Also shown in the first housing member 20 are the first optical window 213, an air bladder exit port 344, the top portion 43 of a sample storage well 41 (see FIG. 1G), a cap latch 70, and a sample inlet portion 40, which comprises the elements of the cartridge that interact with the cap 50. Some embodiments of the cartridge provide a good seal between the cap and the sample inlet portion 40, without a cap latch 70, depending on the robustness of the hinged attachment of the cap. An advantage to having a robust hinged attachment and no cap latch is the greater space provided at the sample storage well, for accommodating the heel of a baby or a large adult finger. The first housing member 20 also reveals the following hidden details: a first portion 87' of a capillary break 87 (see FIG. 1F); an optical chamber inlet conduit groove 219; and an optical chamber overflow conduit groove 229. These hidden elements are show more clearly in FIG. 1B, which illustrates the bottom view of the first housing member 20 of the cartridge 10.

Still referring to FIG. 1A, is a double-sided sticky gasket 100, comprising several cut-outs, which are described in Table 1. Below gasket 100 is the second housing member 30, showing the following elements: a sample storage conduit entrance 81; a sample storage conduit groove 85; the second portion 87" of the capillary break 87; an air bladder cavity 342; a waste receptacle cavity 231; and an illustration of the hidden second optical window 215.

Shown in FIG. 1C is the bottom view of the first housing member shown in FIG. 1B, overlaid by and in alignment with the gasket 100 shown in FIG. 1A. Shown in FIG. 1D is a top view of the second housing member 30 of the cartridge shown in FIG. 1A, illustrating the hidden second optical window 215, and a waste receptacle vent 233. Shown in FIG. 1E is the top view of the second housing member 30 shown in FIG. 1D, overlaid by and in alignment with the gasket 100 shown in FIG. 1A.

Shown in FIG. 1F is a top view of the cartridge 10 shown in FIG. 1A, with the cap 50 in a fully closed position. Illustrated in FIG. 1G is a first cross-sectional view through the cartridge shown in FIG. 1F along line G-G, showing the sample storage well 41, the sample storage conduit entrance 81, and the sections 87' and 87" of the capillary break 87 (see hidden view in FIG. 1F). Shown in FIG. 1H is a second cross-sectional view through the cartridge shown in FIG. 1F along line H-H, showing the sample storage conduit entrance 81, mating with the bottom portion 45 of the sample storage well 41. This mating aspect is better illustrated in FIG. 5J, regarding cartridge 10*b*

Shown in FIG. 1J is a perspective view of the cartridge shown in FIG. 1F. Shown in FIG. 1K is a front view of the cartridge shown in FIG. 1F. Shown in FIG. 1L is a right side view of the cartridge shown in FIG. 1F. The parts shown are described in Table 1.

Figure 2B:
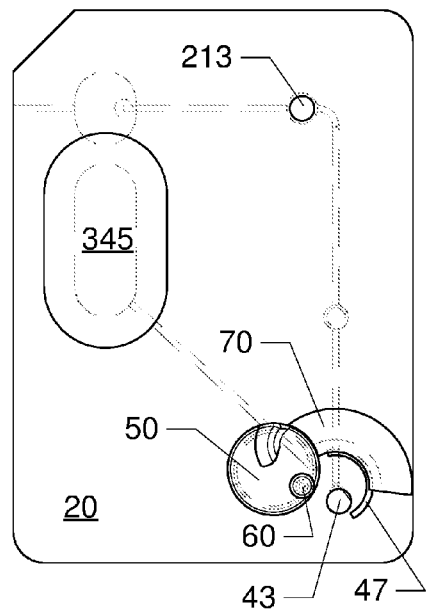
FIG. 2B is a top view of the cartridge 10 shown collectively in FIGS. 1A-1L, with the cap 50 in a fully open position.
Figure 2C:
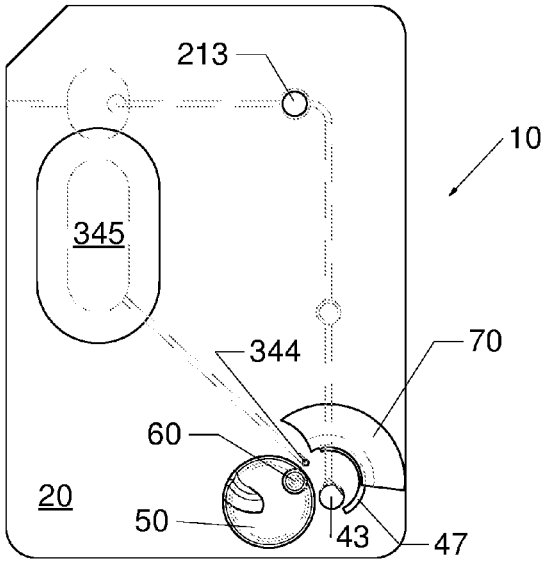
FIG. 2C is a top view of the cartridge 10 shown collectively in FIGS. 1A-1L, with the cap 50 in a partly open position.
Figure 2D:
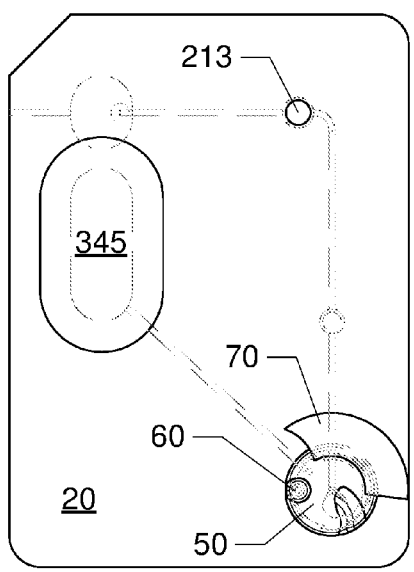
FIG. 2D is a top view of the cartridge 10 shown collectively in FIGS. 1A-1L, with the cap 50 in a fully closed position.

Shown in FIG. 2A is a top view of the cartridge 10 shown collectively in FIGS. 1A-1L, with the cap 50 and pin 60 hidden. Shown in FIG. 2B is a top view of the cartridge 10 shown collectively in FIGS. 1A-1L, with the cap 50 in a fully open position. Shown in FIG. 2C is a top view of the cartridge shown collectively in FIGS. 1A-1L, with the cap 50 in a partly open position. Shown in FIG. 2D is a top view of the cartridge 10 shown collectively in FIGS. 1A-1L, with the cap 50 in a fully closed position.

More details of the sample inlet portion 40 and its association with the cap 50 are illustrated in FIG. 3A, which is a perspective view of the cartridge shown in FIG. 2A. Shown in FIG. 3B is a detailed view of detail B of the cartridge shown in FIG. 3A. Shown in FIG. 3C is a perspective view of the cartridge 10 with the cap 50 engaged. Shown in FIG. 3D is a detailed view of detail D of the cartridge shown in FIG. 3C.

The details of the cap 50 are illustrated in FIG. 4A to FIG. 4G. Shown in FIG. 4A is a top view of the cap 50 shown in FIG. 3C. Shown in FIG. 4B is a perspective view of the cap 50 shown in FIG. 4A. Shown in FIG. 4C is a front view of the cap 50 shown in FIG. 4A. Shown in FIG. 4D is a right side view of the cap 50 shown in FIG. 4A. Shown in FIG. 4E is a bottom view of the cap 50 shown in FIG. 4A. Shown in FIG. 4F is a perspective view of the cap 50 shown in FIG. 4E. Shown in FIG. 4G is a cross-sectional view through the cap 50 shown in FIG. 4E along line G-G, showing the cap recess 55.

Shown in FIG. 5A is an exploded view of the disposable cartridge 10*b* for measuring a property of a sample, the cartridge having a rapid sample metering system, according to a second embodiment of the cartridge. This embodiment is similar to the first embodiment of the cartridge 10, and illustrated collectively in FIG. 1A to FIG. 4G, and accordingly, elements common to them share common reference numerals. For some elements, the letter "b" is appended to the end of the reference numerals, in order to indicate that the elements are part of the second embodiment of the cartridge. A first difference between the first (10) and second (10*b*) embodiments of the cartridge is shape of the cap 50 is circular and the shape of cap 50*b* is elliptical. It should be understood that these are preferred embodiments, and the shape is not limited to being circular or elliptical. Another non limiting example is an oval shape that is not elliptical. An advantage of an ellipse, having a major radius and a minor radius, is that it is equivalent to a circle having a radius equal to the major radius of the ellipse, in the context of space between the latch 70*b* and the pin hole 61*b*, whereby the pin hole is located at one end of the major axis of the ellipse. The larger space, illustrated in FIG. 6B (compare with illustration in FIG. 2B), is useful for accommodating larger fingers, if blood is obtained from a pin prick. A second difference is that the pin 60*b* is an integral part of the cap 50*b*. A third difference is that the detection system in the first embodiment of the cartridge is optical or spectrophotometric, whereas the detection system in the second embodiment is electrochemical or biosensors. A person of ordinary skill will appreciate that other embodiments of the cartridge can have either or both of the aforementioned detection systems.

Shown in FIG. 5B is a bottom view of the first housing member 20*b* of the cartridge shown in FIG. 5A. Shown in FIG. 5C is the bottom view of the first housing member 20*b* shown in FIG. 5B, overlaid by and in alignment with the gasket 100*b* shown in FIG. 5A. Shown in FIG. 5D is a top view of the second housing member 30*b* of the cartridge shown in FIG. 5A. Shown in FIG. 5E is the top view of the second housing member 30*b* shown in FIG. 5D, overlaid by and in alignment with the gasket 100*b* shown in FIG. 5A.

Shown in FIG. 5F is a top view of the cartridge 10*b* shown in FIG. 5A, with the cap 50*b* in a fully closed position. Shown in FIG. 5G is a first cross-sectional view through the cartridge 10*b* shown in FIG. 5F along line G-G. Shown in FIG. 5H is a second cross-sectional view through the cartridge 10b shown in FIG. 5F along line H-H. Shown in FIG. 5J is a detailed view of detail J of the cartridge 10b shown in FIG. 5H, illustrating the fluid connection between the air bladder groove 343 and the sample well 41b, via the air bladder exit port 344b, and the cap recess 55b. The arrangement of the bottom 45b of the sample storage well 41b with the sample storage conduit entrance 81b, is also illustrated. Shown in FIG. 5K is a front view of the cartridge 10b shown in FIG. 5F, and shown in FIG. 5L is a perspective view of the cartridge 10b shown in FIG. 5F.

Shown in FIG. 6A is a top view of the cartridge 10b shown collectively in FIGS. 5A-5L, with the cap 50b hidden. Shown in FIG. 6B is a top view of the cartridge 10b shown collectively in FIGS. 5A-5L, with the cap 50b in a fully open position. Shown in FIG. 6C is a top view of the cartridge 10b shown in FIG. 6B, with the cap 50b in a partially open position. Shown in FIG. 6D is a top view of the cartridge 10b shown collectively in FIGS. 6B-6C, with the cap 50b in a fully closed position. Shown in FIG. 6E is a cross-sectional view of cartridge 10b shown in FIG. 6D along line E-E. Shown in FIG. 6F is a detailed view of detail F of cartridge 10b shown in FIG. 6E, showing a snap-fit mechanism for engaging the cap 50b in the cartridge 10b shown collectively in FIGS. 6B-6C. Description of the elements shown is provided in Table 1.

Shown in FIG. 7A is a perspective view of the cartridge 10b shown in FIG. 6A. Shown in FIG. 7B is a detailed view of detail B of the cartridge shown in FIG. 7A, showing details of the sample inlet portion 40b. Shown in FIG. 7C is a perspective view of the cartridge 10b shown in FIGS. 5F and 6D. Shown in FIG. 7D is a detailed view of detail D of the cartridge shown in FIG. 7C. Description of the elements shown is provided in Table 1.

Shown in FIG. 8A is a top view of the cap 50b shown in FIGS. 7C-7D. Shown in FIG. 8B is a perspective view of the cap 50b shown in FIG. 8A. Shown in FIG. 8C is a front view of the cap 50b shown in FIG. 8A. Shown in FIG. 8D is a right side view of the cap 50b shown in FIG. 8A. Shown in FIG. 8E is a bottom view of the cap 50b shown in FIG. 8A. Shown in FIG. 8F is a perspective view of the cap 50b shown in FIG. 8E. Shown in FIG. 8G is a cross-sectional view through the cap 50b shown in FIG. 8E along line G-G, showing the cap recess 55b and the pin snap fit lip 65b. The means provided for hingedly attaching the cap are examples only, and other means are considered within the scope of the invention.

Measurement of any property of a liquid sample, for example glucose concentration or prothrombin time, can be considered as examples for illustrating the use of the cartridge. In the illustration, the preferred embodiment of the cartridge 10b will be used. In general terms, the present invention is a disposable cartridge for metering a sample for measuring a property of the sample, the cartridge comprising: 1) a housing comprising a first housing member 20b and a second housing member 30b, bonded together by a double-sided sticky gasket 100b; 2) a cap 50b having a top side 51b, an underside 52b, a sweeping cap edge 58b for skimming off excess sample, and a cap recess 55b in the underside of the cap for creating a closed air passage illustrated in FIG. 5J; 3) a pin 60b for hingedly attaching the cap 50b to an inlet portion 40b of the cartridge. The sample inlet portion 40b comprises: a) the top 43b of a sample storage well 41b for receiving the sample; b) the sample storage well 41b for storing a portion of the sample; c) a sliding surface 49b for frictionally engaging the cap 50b; d) a hole 61b for receiving the pin 60b for hingedly attaching the cap 50b to the sample inlet portion 40b; e) a sample overflow well 47b for receiving the excess sample during the period of closing the cap; f) a cap latch 70b for facilitating a sealed configuration of the sample inlet portion 40b of the cartridge; and g) an air bladder exit port 344b in fluid communication with an air bladder 340b. The cartridge 10b further comprises: 4) the air bladder 340b for providing pressurized air to the air bladder exit port 344b; 5) a capillary break 87b for stopping sample flow, the flow being facilitated by capillary action; 6) a detection chamber (a conduit over the active area 323 of a biosensor, of biosensor array 330; in the case of cartridge 10, the detection chamber is the optical chamber 211 [see FIG. 1J]) for generating a signal used the calculate a property of the sample; 7) a post capillary break conduit 91b providing fluid communication between the capillary break 87B and a mixing chamber 89; 8) a waste receptacle 235b for receiving fluid flowing beyond the detection chamber; and 9) a vent 233b for relieving pressure in the waste receptacle 235b. In some embodiments of the cartridge, the sample overflow well 47b is optional. In these embodiments (not shown), as an example, the sweeping portion 53b of the cap 50b comprises a recess disposed in the underside of the cap in front of the sweeping edge 58b, for holding the excess sample.

The cartridge is adjustable between an unsealed (also referred to as a partially open position when describing FIG. 6C, and a fully open position when describing FIG. 6B) configuration and a sealed (also referred to as a fully closed position when describing FIG. 6D) configuration. In the unsealed configuration, and not in the sealed configuration, the sample storage well 41b is configured to receive the sample, and the air bladder exit port 344b is either exposed to the atmosphere (see FIG. 6C) or covered by the cap 50b (see FIG. 6B). In the sealed configuration, and not in the unsealed configuration, the cap recess 55b facilitates provision of a closed air passage connecting the air bladder exit port 344b and the sample storage well 41b for transferring pressurized air from the air bladder exit port 344b to the sample storage well 41b, illustrated in FIG. 5J. As the cartridge is adjusted from the unsealed configuration to the sealed configuration, the sweeping cap edge 58b skims off excess sample above the top 43b of the sample storage well 41b, whereby the volume of sample in the cartridge in the sealed configuration is equivalent to the volume measured from the top 43b of the sample storage well 41b to the capillary break 87b. The sample storage well also comprises a bottom 45b of the sample storage well 41b. In this embodiment, the top 43b is substantially larger than the bottom 45b. The advantage of having a larger top 43b is for transferring a drop of blood from a body part, for example a finger, to the sample storage well 41b. In the case of a small infant, a heel is a preferred body part. The size of the smaller bottom 45b is preferably similar to the size of the sample storage conduit entrance 81b, for facilitating blood flow by capillary action.

Once the cartridge is in the sealed configuration, the cartridge is ready to be inserted into a slot or receptor of an analyzer. The analyzer detection system comprises one or more of, optical, spectrophotometric, fluorescence, chemiluminescence, electrochemical, biosensor, amperometric, potentiometric or conductimetric technology. However, these are just examples and other detection systems are considered to be within the scope of the present invention. These detection systems are known to a person skilled in the art and for the sake of brevity, will not be discussed here. Another feature of the analyzer is a means for depressing the flexible member 345b of the cartridge 10b, for generating pressurized air for advancing the sample towards the detection chamber. This is facilitated by the fluid connection between an air bladder exit port 344b and a sample well 41b, via a cap recess 55b, illustrated in FIG. 5J. The flexible member can also be repeatedly depressed and released causing the blood to move forward and backward, in order to dissolve one or more dry reagent in the blood sample, and provide better mixing of sample and reagent.

A method for measuring a property of a blood sample, comprises some or all of the following steps, not necessarily in the sequence given. One step is providing a cartridge (for example, one shown as 10b) and an analyzer comprising a slot or receptor for receiving a cartridge, the cartridge comprising one or more dry reagent deposited at one or more points in the capillary break 87b or in the post capillary break conduit disposed between the capillary break 87b and the detection system. Cartridge 10b comprises an optional mixing chamber 89, and a post capillary break conduit 91b, which defines the conduit between the capillary break 87b and the mixing chamber 89, illustrated in FIG. 5F. In some cartridge embodiments, the one or more reagent is deposited in the mixing chamber 89. Dry thromboplastin is an example of a reagent, which is used for measuring prothrombin time.

In another step, the cartridge is placed flat on a table, and the cap 50b is rotated in a clockwise direction until the cap 50b hits the latch 70b, adjusting the cartridge 10b in the fully unsealed configuration, as illustrated in FIG. 6B. It should be noted that in this configuration, the cap 50b creates maximum opening of the top 43b of the sample storage well 41b, and at the same time, the cap 50b covers the air bladder exit port 344b, thereby mitigating flow of blood into the air bladder exit port 344b.

In another step, a finger of the patient is pricked, and after a drop of blood is allowed to develop on the finger, following best practice procedures, the blood is allowed to touch the top portion 43b of the sample storage well 41b. The blood is drawn into the storage well 41b and into the sample storage conduit 83b, up to the capillary break 87b. Slightly excess blood is applied so that the blood sample bulges above the top portion 43b of the sample storage well 41b.

In another step, the cap 50b is rotated counterclockwise into the recess 73b of the cap latch 70b, as illustrated in FIG. 6D. Details of the sample inlet portion 40b and its association with cap 50b are illustrated collectively in FIGS. 7A-7D. During the cap movement, the sweeping cap edge 58b skims off excess blood, which is dumped into the sample overflow well 47b, or held in a recess disposed at the underside of the cap in front of the sweeping cap edge 58b. The volume of the metered blood is the volume of the sample storage well 41 and the volume of the sample storage conduit 83b. When the cap 50b is fully inserted into cap latch recess 73b, the cartridge in the sealed configuration.

In another step, the cartridge in the sealed configuration is inserted in the slot or receptor of the analyzer (not shown). The steps following cartridge insertion are automatically performed by the analyzer, and comprise depression of the flexible member 345b. The flexible member 345b can also be repeatedly depressed and released causing the blood to move forward and backward, in order to dissolve the dry one or more reagent in the blood sample. Depression or (repeated depression followed by release) of the flexible member 345b may be performed by a small stepper motor mounted on the receptor of the analyzer, but other means may be used that is known by a person skilled in the art. In the case of cartridge 10b, having an optional mixing chamber 89, the turbulence created as the blood sample flows into the mixing chamber 89 is sufficient to dissolve the one or more reagent, depending on the nature of the one or more reagent. It is known that some lyophilized reagents in relatively small quantities will dissolve almost immediately after the blood sample makes contact with the lyophilized substance, for example thromboplastin, used for measuring prothrombin time. It is also known that some reagents can be coated on the walls of a conduit, and more mixing is required to dissolve the reagents from the conduit walls.

In accordance with an aspect of an embodiment of the present invention, there is provided a disposable cartridge for metering a sample for measuring a property of the sample. The cartridge comprises a cap having a sweeping edge for skimming off excess sample, a top side and an underside comprising a flat surface and a recess. The cartridge also comprises a sample inlet portion having: a sample storage well for storing a portion of the sample, the storage well comprising a top portion for receiving the sample and a bottom portion for releasing sample; a sliding surface for frictionally engaging the flat surface of the underside of the cap; a hole for receiving a pin for hingedly attaching the cap; and a sample storage conduit for receiving some of the sample from the bottom portion of the sample storage well, the sample storage conduit terminating at a capillary break; a detection chamber for receiving sample from the capillary break for generating a signal used to calculate the property of the sample; and an air bladder having an arrangement with the air bladder exit port and the cap recess when the cartridge is in the sealed configuration for providing pressurized air to the sample storage well for urging the sample into the detection chamber. When the cartridge is in the sealed configuration, the volume of sample is defined by the combined volumes of the sample storage well and the sample storage conduit. In some embodiments of the cartridge, the top portion of the sample storage well is substantially larger than the bottom portion of the sample storage well. In some embodiments of the cartridge, the pin is an integral part of the cap and in other embodiments, the pin is a separate element. In other embodiments of the cartridge, at least one of the sample storage conduit and the capillary break comprises at least one reagent. Other embodiments of the cartridge comprise a mixing chamber positioned between the capillary break and the detection chamber, the mixing chamber optionally comprising at least one reagent.

In accordance with another aspect of an embodiment of the present invention, there is provided a disposable cartridge for metering a sample for measuring a property of the sample, the cartridge comprising a cap and a housing. The cap comprises a sweeping edge for skimming off excess sample, a top side, and an underside, the underside comprising a flat surface and a recess enclosed by the flat surface. The housing comprises: a sample storage well for storing a portion of the sample, the storage well comprising a top portion for receiving the sample and a bottom portion for releasing sample; a hole for receiving a pin for hingedly attaching the cap to the housing; a sample storage conduit for receiving some of the sample from the bottom portion of the sample storage well, the sample storage conduit terminating at a capillary break; a detection chamber for receiving sample from the capillary break and for generating a signal used to calculate the property of the sample; an air bladder exit port; an air bladder having an arrangement with the air bladder exit port for providing pressurized air to the sample storage well for urging the sample into the detection chamber; and a vent for relieving pressure in the detection chamber. The cartridge is adjustable between an unsealed configuration and the sealed configuration, facilitated by the pin. In the unsealed configuration, and not in the sealed configuration, the sample storage well is configured to receive the sample. In the sealed configuration, and not in the unsealed configuration, the cap recess facilitates provision of a closed air passage connecting the air bladder exit port and the sample storage well for communicating the pressurized air from the air bladder exit port to the sample storage well. The volume of sample in the cartridge in the sealed configuration is equivalent to the volume measured from the top portion of the sample storage well to the capillary break. Some embodiments further comprise a latch for securing the cap when the cartridge is in a sealed configuration, and some embodiments comprise a sample overflow well for receiving excess sample. In some embodiments, instead of the overflow well, there is a groove disposed at the underside of the cap in front of the sweeping edge of the cap, for holding the excess sample.

In accordance with yet another aspect of an embodiment of the present invention, there is provided a system for metering a sample for measuring a property of the sample. The system comprises a cartridge and an analyzer. The cartridge comprises a cap and a housing. The cap comprises a sweeping edge for skimming off excess sample, a top side, and an underside, the underside having a recess. The housing comprises: a sample storage well for storing a portion of the sample, the storage well comprising a top portion for receiving the sample and a bottom portion for releasing sample; a hole for receiving a pin for hingedly attaching the cap to the housing; a sample storage conduit for receiving some of the sample from the bottom portion of the sample storage well, the sample storage conduit terminating at a capillary break; a detection chamber for receiving sample from the capillary break and for providing signal to the analyzer for measuring the property of the sample; an air bladder exit port; an air bladder having an arrangement with the air bladder exit port for providing pressurized air to the sample storage well for urging the sample into the detection chamber; and a vent for relieving pressure in the detection chamber. The analyzer comprises: a receptor for receiving the cartridge; a processor for controlling the analyzer; means for activating the air bladder, for example a stepper motor and means for receiving the signal from the detection chamber and calculating the property of the sample. The description provides as examples of detection technology, optical measurement and electrochemical sensors, but these are examples only and other forms of generating signals and receiving generated signals for measuring an analyte are considered to be within the scope of the present invention.

While the above description provides example embodiments, it will be appreciated that the present invention is susceptible to modification and change without departing from the fair meaning and scope of the accompanying claims. Accordingly, what has been described is merely illustrative of the application of aspects of embodiments of the invention. Numerous modifications and variations of the present invention are possible in light of the above teachings. It is therefore to be understood that within the scope of the appended claims, the invention may be practiced otherwise than as specifically described herein. Furthermore, the discussed combination of features might not be absolutely necessary for the inventive solution.

I claim:

1. A disposable cartridge for metering a sample for measuring a property of the sample, the cartridge comprising:
    a cap having a sweeping edge for skimming off excess sample, a top side and an underside, the underside comprising a flat surface and a recess;
    a sample inlet portion comprising:
        a sample storage well for storing a portion of the sample, the storage well comprising a top portion for receiving the sample and a bottom portion for releasing sample;
        a sliding surface for frictionally engaging the flat surface of the underside of the cap;
        a hole for receiving a pin for hingedly attaching the cap;
        a sample overflow well for receiving the excess sample;
        an air bladder exit port; and
        a latch for securing the cap when the cartridge is in a sealed configuration;
    a sample storage conduit for receiving some of the sample from the bottom portion of the sample storage well, the sample storage conduit terminating at a capillary break;
    a detection chamber for receiving sample from the capillary break and for generating a signal used to calculate the property of the sample; and
    an air bladder having an arrangement with the air bladder exit port and the cap recess when the cartridge is in the sealed configuration for providing pressurized air to the sample storage well for urging the sample into the detection chamber;
    whereby when the cartridge is in the sealed configuration, the volume of sample is defined by the combined volumes of the sample storage well and the sample storage conduit.

2. The cartridge according to claim 1, wherein the top portion of the sample storage well is substantially larger than the bottom portion of the sample storage well.

3. The cartridge according to claim 1, wherein the pin is an integral part of the cap.

4. The cartridge according to claim 1, wherein at least one of the sample storage conduit and the capillary break comprises at least one reagent.

5. The cartridge according to claim 1, wherein the cartridge further comprises a mixing chamber positioned between the capillary break and the detection chamber.

6. The cartridge according to claim 5, wherein the mixing chamber comprises at least one reagent.

7. A disposable cartridge for metering a sample for measuring a property of the sample, the cartridge comprising a cap and a housing:
    the cap comprising:
        a sweeping edge for skimming off excess sample;
        a top side;
        an underside having a flat surface; and
        a recess enclosed by the flat surface;
    the housing comprising:
        a sample storage well for storing a portion of the sample, the storage well comprising a top portion for receiving the sample and a bottom portion for releasing sample;
        a hole for receiving a pin for hingedly attaching the cap to the housing;
        a sample storage conduit for receiving some of the sample from the bottom portion of the sample storage well, the sample storage conduit terminating at a capillary break;
        a detection chamber for receiving sample from the capillary break and for generating a signal used to calculate the property of the sample;
        an air bladder exit port;
        an air bladder having an arrangement with the air bladder exit port for providing pressurized air to the sample storage well for urging the sample into the detection chamber; and a vent for relieving pressure in the detection chamber;
wherein
the cartridge is adjustable between an unsealed configuration and the sealed configuration, facilitated by the pin;
in the unsealed configuration, and not in the sealed configuration, the sample storage well is configured to receive the sample; and,
in the sealed configuration, and not in the unsealed configuration, the cap recess facilitates provision of a closed air passage connecting the air bladder exit port and the sample storage well for communicating the pressurized air from the air bladder exit port to the sample storage well;
whereby the volume of sample in the cartridge in the sealed configuration is equivalent to the volume measured from the top portion of the sample storage well to the capillary break.

8. The cartridge according to claim 7, further comprising a groove disposed at the underside of the cap in front of the sweeping edge of the cap, for holding the excess sample.

9. The cartridge according to claim 7, further comprising a latch for securing the cap when the cartridge is in the sealed configuration.

10. The cartridge according to claim 7, wherein the top portion of the sample storage well is substantially larger than the bottom portion of the sample storage well.

11. The cartridge according to claim 7, wherein the pin is an integral part of the cap.

12. The system according to claim 7, wherein the cartridge space between the sample storage conduit and the detection chamber comprises dry thromboplastin, the sample is blood and the property of the blood is prothrombin time.

13. The cartridge according to claim 7, wherein at least one of the sample storage conduit and the capillary break comprises at least one reagent.

14. The cartridge according to claim 7, wherein the cartridge further comprises a mixing chamber positioned between the capillary break and the detection chamber.

15. The cartridge according to claim 14, wherein the mixing chamber comprises at least one reagent.

16. A system for metering a sample for measuring a property of the sample, the system comprising a cartridge and an analyzer:
a cartridge comprising a cap and a housing:
the cap comprising:
a sweeping edge for skimming off excess sample;
a top side; and
an underside, the underside having a recess;
the housing comprising:
a sample storage well for storing a portion of the sample, the storage well comprising a top portion for receiving the sample and a bottom portion for releasing sample;
a hole for receiving a pin for hingedly attaching the cap to the housing;
a sample storage conduit for receiving some of the sample from the bottom portion of the sample storage well, the sample storage conduit terminating at a capillary break;
a detection chamber for receiving sample from the capillary break and for providing signal to the analyzer for measuring the property of the sample;
an air bladder exit port;
an air bladder having an arrangement with the air bladder exit port for providing pressurized air to the sample storage well for urging the sample into the detection chamber; and
a vent for relieving pressure in the detection chamber;
the analyzer comprising:
a receptor for receiving the cartridge;
a processor for controlling the analyzer;
means for activating the air bladder; and
means for receiving the signal from the detection chamber and calculating the property of the sample.

17. The system according to claim 16, wherein the housing further comprises a latch for securing the cap when the cartridge is in a sealed configuration, wherein in the sealed configuration the cap recess facilitates provision of a closed air passage connecting the air bladder exit port and the sample storage well for communicating the pressurized air from the air bladder exit port to the sample storage well.

18. The system according to claim 16, wherein the housing further comprises a sample overflow well for receiving the excess sample.

19. The system according to claim 16, wherein the top portion of the sample storage well is substantially larger than the bottom portion of the sample storage well.

20. The system according to claim 16, wherein the cartridge space between the sample storage conduit and the detection chamber comprises dry thromboplastin, the sample is blood and the property of the blood is prothrombin time.

* * * * *